US011439728B2

(12) United States Patent
Shete et al.

(10) Patent No.: US 11,439,728 B2
(45) Date of Patent: Sep. 13, 2022

(54) PROCESS FOR COATING A BIOMEDICAL IMPLANT WITH A BIOCOMPATIBLE POLYMER AND A BIOMEDICAL IMPLANT THEREFROM

(71) Applicant: COUNCIL OF SCIENTIFIC & INDUSTRIAL RESEARCH, New Delhi (IN)

(72) Inventors: Abhijit Pravin Shete, Pune (IN); Anuya Amol Nisal, Pune (IN); Ashish Kishore Lele, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/495,683

(22) PCT Filed: Mar. 23, 2018

(86) PCT No.: PCT/IN2018/050163
§ 371 (c)(1),
(2) Date: Sep. 19, 2019

(87) PCT Pub. No.: WO2018/173074
PCT Pub. Date: Sep. 27, 2018

(65) Prior Publication Data
US 2020/0054787 A1 Feb. 20, 2020

(30) Foreign Application Priority Data
Mar. 23, 2017 (IN) .............................. 201711010187

(51) Int. Cl.
*A61L 24/00* (2006.01)
*A61L 27/34* (2006.01)
(Continued)

(52) U.S. Cl.
CPC ............... *A61L 27/34* (2013.01); *A61L 27/06* (2013.01); *A61L 27/10* (2013.01);
(Continued)

(58) Field of Classification Search
CPC .................................................. A61L 2420/02
See application file for complete search history.

(56) References Cited

U.S. PATENT DOCUMENTS 3,971,316 A * 7/1976 Schank .................. B41N 1/003
430/303
7,316,710 B1 * 1/2008 Cheng ....................... A61F 2/91
623/1.15
(Continued)

FOREIGN PATENT DOCUMENTS

WO WO2017093181 6/2017
WO WO-2017093181 A1 * 6/2017 ........... C08G 81/024

OTHER PUBLICATIONS

Park et al. Preparation and characterization of polyurethane/nylon 6 nanofiber/ silicone film composites via electrospinning and dip-coating. Fibers and Polymers 2012, vol. 13, No. 3 pp. 339-345 (Year: 2012).*
(Continued)

*Primary Examiner* — Cachet I Proctor
(74) *Attorney, Agent, or Firm* — Blank Rome LLP (57) ABSTRACT

The present invention disclosed a process to coat the surface of flexible polymeric implant with biocompatible polymer such that the coating does not crack when the implant is subjected to mechanical forces such as tension, torsion or bending while retaining the inherent properties of the coated polymer.

20 Claims, 7 Drawing Sheets

(51) Int. Cl.

| | |
|---|---|
| A61L 27/36 | (2006.01) |
| A61L 29/00 | (2006.01) |
| A61L 29/08 | (2006.01) |
| A61L 31/00 | (2006.01) |
| A61L 31/10 | (2006.01) |
| A61L 27/50 | (2006.01) |
| A61L 29/14 | (2006.01) |
| A61L 31/14 | (2006.01) |
| A61L 27/06 | (2006.01) |
| A61L 27/10 | (2006.01) |
| A61L 27/40 | (2006.01) |
| A61L 29/02 | (2006.01) |
| A61L 29/12 | (2006.01) |
| A61L 31/02 | (2006.01) |
| A61L 31/12 | (2006.01) |
| A61L 27/54 | (2006.01) |
| A61L 29/16 | (2006.01) |
| A61L 31/16 | (2006.01) |
| D01D 5/00 | (2006.01) |
| D01F 4/02 | (2006.01) |

(52) U.S. Cl.
CPC ....... *A61L 27/3604* (2013.01); *A61L 27/3641* (2013.01); *A61L 27/40* (2013.01); *A61L 27/505* (2013.01); *A61L 27/54* (2013.01); *A61L 29/005* (2013.01); *A61L 29/02* (2013.01); *A61L 29/085* (2013.01); *A61L 29/12* (2013.01); *A61L 29/143* (2013.01); *A61L 29/16* (2013.01); *A61L 31/005* (2013.01); *A61L 31/022* (2013.01); *A61L 31/026* (2013.01); *A61L 31/10* (2013.01); *A61L 31/12* (2013.01); *A61L 31/143* (2013.01); *A61L 31/16* (2013.01); *D01D 5/0007* (2013.01); *D01F 4/02* (2013.01); *A61L 2420/02* (2013.01); *A61L 2430/04* (2013.01); *A61L 2430/16* (2013.01); *D10B 2509/00* (2013.01)

(56) References Cited

U.S. PATENT DOCUMENTS

| | | | | |
|---|---|---|---|---|
| 2004/0199241 A1* | 10/2004 | Gravett | ............ | A61L 31/14 623/1.13 |
| 2005/0142163 A1* | 6/2005 | Hunter | ............ | A61P 1/00 424/423 |
| 2006/0134160 A1* | 6/2006 | Troczynski | ............ | A61L 27/56 424/422 |
| 2007/0207186 A1* | 9/2007 | Scanlon | ............ | A61F 2/91 424/424 |
| 2010/0070022 A1* | 3/2010 | Kuehling | ............ | A61F 2/82 623/1.16 |
| 2010/0255270 A1* | 10/2010 | Stuebiger | ............ | D06M 15/643 442/139 |
| 2011/0054595 A1* | 3/2011 | Landy | ............ | A61L 31/082 623/1.39 |
| 2011/0282437 A1* | 11/2011 | Warner | ............ | A61F 2/915 623/1.44 |
| 2013/0156844 A1* | 6/2013 | Kaplan | ............ | A61L 15/44 424/445 |
| 2014/0010950 A1* | 1/2014 | Mangiardi | ............ | A61L 31/10 427/2.25 |
| 2015/0202351 A1* | 7/2015 | Kaplan | ............ | A61L 31/10 607/116 |
| 2015/0285335 A1* | 10/2015 | Mitsutomi | ............ | F16G 5/06 156/137 |

OTHER PUBLICATIONS

Liu et al. positive vascular scaffold combining natural spot fibers physically cross-linked hydrogel with copper wire induced whose structure. Journal of the mechanical behavior biomedical materials. 61 (2016) pp. 12-25 (Year: 2016).*

Borkner et al., "Surface Modification of Polymeric Biomaterials Using Recombinant Spider Silk Proteins", ACS Biomaterials Science & Engineering, pp. 1-8.

Park et al., "Preparation and Characterization of (polyurethane/nylon-6) Nanofiber/(silicone) Film Composites via Electrospinning and Dip-coating", Fibers and Polymers, 2012, vol. 13, No. 3, pp. 339-345.

Abdal-hay et al., "In vitro bioactivity of titanium implants coated with bicomponent hybrid biodegradable polymers", J Sol-Gel Sci Technol, 2012,64, pp. 756-764.

Sato et al., "Small-diameter vascular grafts of Bombyx mori silk fibroin prepared by a combination of electrospinning and sponge coating", Material Letters, 64, 2010, pp. 1786-1788.

Softer et al., "Silk-Based Electrospun Tubular Scaffolds for Tissue-Engineered Vascular Grafts", J Biomater Sci Polym Ed., 2008; 19(5): pp. 653-664.

Park et al., "Alleviation of capsular formations on silicone implants in rats using biomembrane-mimicking coatings", Acta Biomaterialia 10,2014, pp. 4217-4225.

Rudolph et al., "Surface Modification of Biodegradable Polymers toward Better Biocompatibility and Lower Thrombogenicity", PLOS One, DOI:10.1371/journal.pone.0142075, Dec. 7, 2015, pp. 1-17.

Strohbach et al., "Polymers for Cardiovascular Stent Coatings", International Journal of Polymer Science, vol. 2015, pp. 1-11.

* cited by examiner

Fig. 1

Bend by ~180°
three times

PROCESS FOR COATING A BIOMEDICAL IMPLANT WITH A BIOCOMPATIBLE POLYMER AND A BIOMEDICAL IMPLANT THEREFROM

RELATED APPLICATIONS

This application is a national phase application of PCT/IN2018/050163, filed Mar. 23, 2018, which claims priority to Indian Application No. 201711010187, filed Mar. 23, 2017. The entire contents of those applications are incorporated herein by reference.

FIELD OF THE INVENTION

The present invention relates to a process for coating a biomedical implant. More particularly, the present invention relates to a process for coating an implant with a biocompatible polymer by using a sequential dip coating and electrospinning process.

BACKGROUND OF THE INVENTION

Medical devices and biomedical implants are today used in various applications and their performance is directly linked to the health of the patient. These devices can be in direct or indirect contact with the patient body and/or body fluids for time periods as short as few hours or as long as many years. Also, these devices can sometimes cause either minor or major discomfort to the patient. For example, catheters are one of the most commonly used medical devices in hospitals for removal of bodily fluids. Indwelling catheters are catheters that reside in the urinary bladder and the time period of usage may very from few hours to few months depending on patient condition. The outer surface of the tubes of these catheters are frequently known to have problems due to bacterial biofilm formation leading to further complications such as urinary tract infection. On the other hand, there could be implants that are subcutaneously implanted in the body like silicone breast implants or metallic or polymer stents. Silicone breast implants are frequently used in breast augmentation surgeries and also in breast reconstruction surgery immediately after total mastectomy and these implants stay in the body for many years. The injured surgical tissue surrounding the implant is known to initiate localised non-specific inflammatory response. This sometimes results in the formation of a constrictive fibrotic capsule post-implantation, known as capsular contracture, which results in firmness, deformity and pain in early stages ultimately leading to device failure and implant-removal surgery. Similar problems have also been observed in case of polymeric materials used in cardiology applications. For examples, implantation of stents can result in in-stent restenosis, late stent-thrombosis, and hypersensitivity reactions (Strohbach & Busch et al., *International Journal of Polymer Science*, Volume 2015, Article ID 782653, 11 pages).

One of the approaches to solving these problems is surface modification of these implants. Surface coatings are thus, a rapidly evolving field for biomedical implants. For example, most catheters today are manufactured with an antimicrobial coating on the outer surface that prevents bacterial film formation. More recently, there have also been efforts to modify the surface of the silicone breast implant to improve its biocompatibility (Park et al. *Acta Biomaterialia;* 2014, 10, pp 4217-4225). Drug eluting polymer coated stents also have shown to significantly reduce restenosis as compared to bare metal stents (Rudolph et al. 2015 *PLoS One.* 2015; 10(12):e0142075).

The stability of the coating during use is an important aspect for these applications. For example, the PDMS implant undergoes tensile deformation during clinical procedures; one due to handling by the clinicians and also when it is injected with saline solution to increase its size. These mechanical forces can lead to cracking of the coating. Similarly the catheter tubes also undergo bending stresses. Under these circumstances, it is desired that the coating remains intact and does not fail due to cracking. The cracking of the coating may expose the underlying substrate; which may lead to a cascade of unfavourable biological events viz. capsular contracture or bacterial biofilm formation.

Thus, there is a critical need in the field of biomaterial science to develop simple methods for assembly of well-controlled, biocompatible and functionalized biomaterial coatings. In the field, it is common knowledge, to play with the material properties to avoid cracking of final product. The general method implemented is either by addition plasticizers or by blending with other materials or by reinforcement. However, in the particular case of implants, where in they are exposed to a biological environment, the selection of materials has severe restrictions such as biocompatibility, leeching, rate of bioresorption, etc. The unequal interaction of two or more materials with the surrounding media could result in deterioration of properties in the course of time. Further, it is widely known in the field of composites that self-reinforcement increases the toughness of the product (example: self-reinforced polypropylene). Coating polymeric implants with self-reinforced polymer fiber composites has not been explored till date. Self-reinforcement is advantageous since it would not hamper inherent properties of SF such bio-compatibility, thermo-mechanical stability, anti-bacterial activity, bioresorption, etc.

WO2017093181 discloses a medical implant comprising a fiber reinforced silicone comprising (A) a silicone matrix and (B) fibers embedded in the silicone matrix, wherein the fibers comprise a comb polymer having a base polymer and side chains, wherein the base polymer is an organic polymer and the side chains comprise polysiloxanes, wherein the fiber enforced silicone is produced by dip coating and/or electrospinning. The process here involves placing an already electrospun mat onto a dip coated layer of silicone. It further applies another layer of silicone to completely wet the electrospun fibers.

Article titled" "Preparation and characterization of (polyurethane/nylon-6) nanofiber/(silicone) film composites via electrospinning and dip-coating" by CH Park et al. published in *Fibers and Polymers,* 2012, 13(3), pp 339-345 reports on the preparation and characterization of nanofibers and nanofiber/film composites fabricated by electrospinning and dip-coating. The silicone was dried for 5 or 150 min before nanofibers of polyurethane, or nylon-6 were electrospun to the dried/semi-dried silicone film. The resulting nanofiber/film composites were dried for 24 h at 80° C. in a dry oven. The polymers in this study consist of polyurethane, nylon-6, and silicone. They report that the electrospun PU/nylon-6 composite nanofiber by side-by-side electrospinning produced better tensile strength than either of pure PU or nylon-6 nanofibers alone, but it suffered a low tensile strain.

Article titled "In vitro bioactivity of titanium implants coated with bicomponent hybrid biodegradable polymers" by A Abdal-hay et al. published in *Journal of Sol-Gel*

*Science and Technology;* 2012, 64 (3), pp 756-764 reports the effect of different polymer coating layers (PLA and a PCL/PLA hybrid) applied to Ti surfaces on in vitro Ti substrate bioactivity and corrosion resistance. The bicomponent PCL/PLA membrane was applied to a Ti substrate starting with the coating of Ti samples with a porous PLA film layer using a dip-coating technique. This was followed by deposition of electrospun PCL nanofibers onto the Ti substrate, resulting in a PCL/PLA bicomponent hybrid coating layer. In this study, Ti surfaces were modified with organic polymer coatings applied by dip-coating and electrospinning techniques.

US20140010950 discloses devices and methods for the treatment of wounds in luminal vessels and organs, and other vascular abnormalities. In particular, the invention relates to a device and methods for the treatment of perforations, fistulas, ruptures, dehiscence, punctures, incisions, and aneurisms in luminal vessels and organs of a subject. The method of making a device for aneurism and perforation management, comprising: dipping a rigid, stent like body in a biodegradable coating material to form a coated stent like body; and electrospinning fibers of a covering material onto said coated stent like body.

Article titled "Small-diameter vascular grafts of *Bombyx mori* silk fibroin prepared by a combination of electrospinning and sponge coating" by M Sato et al. published in *Materials Letters;* 2010, 64 (16), pp 1786-1788 reports small-diameter grafts made of a silk fibroin by electrospinning. In order to reinforce the electrospun silk fibroin graft (ES), the graft was coated with a silk sponge (ESSC). Physical properties such as a diameter of the electrospun silk fibers were influenced by a concentration of fibroin solution. Ultimate tensile strength (UTS) of the ESSC graft was improved compared to the ES graft. To improve mechanical strength of the electrospun silk graft, it was assembled with a fibroin sponge coating. The silk sponge coating enhanced tensile strength and elastic modulus circumferentially and longitudinally compared to the electrospun silk fibroin graft without the coating.

Article titled "Silk-based electrospun tubular scaffolds for tissue-engineered vascular grafts" by L Soffer et al. published in *J Biomater Sci Polym Ed.;* 2008; 19(5); 653-664 report use of electrospinning to fabricate nonwoven nanofibrous tubular structures from *Bombyx mori* silk fibroin using an all aqueous process. The tubes were prepared for cell studies related to the bioengineering of small diameter vascular grafts. Prior to cell culture, the structures displayed burst strength of 811±77.2 mmHg, sufficient to withstand arterial pressures. The tensile properties were similar to native vessels, with an ultimate tensile strength of 2.42±0.48 MPa and a linear modulus of 2.45±0.47 MPa.

US20130156844 disclosed a method for the controlled assembly of layered silk fibroin coatings using aqueous silk fibroin material. The methods described herein can be used to coat substrates of any material, shape, or size. Importantly, the described methods enable control of the biomaterial surface chemistry, thickness, morphology and structure using layered thin film coatings, or bulk coatings. Furthermore, the methods can be performed in all water and do not require intensive chemical processing enabling controlled entrapment of labile molecules such as, drugs, cytokines, and even cells or viruses to generate functional coatings that can be used in a variety of applications.

Article titled "Surface modification of polymeric biomaterials using recombinant spider silk proteins" by CB Borkner et al. published in *ACS Biomater. Sci. Eng.*, Article ASAP reports a coating with a recombinantly produced spider silk protein as outer layer applied on three selected catheter polymers (polyurethane, polytetrafluoroethylene, silicone) and evaluated based on cell adhesion. The tested cell types, HaCaT keratinocytes (epidermal cells), B50 neuronal cells, $C_2C_{12}$ myoblasts (muscle cells) and BALB/3T3 fibroblasts (connective tissue), exhibited low or no adhesion on the silk-coated materials. The authors in this article also report that they observed small micro or nano cracks on these coatings, when subjected to a bending test.

Biocompatible polymers such as silk fibroin, collagen, etc. have been used for coating applications. Coatings of these polymers on various metallic and polymeric implants have been prepared by a variety of techniques, including dip-coating, electrospinning, plasma spraying, sol-gel, RF sputtering, detonation gun coating, high velocity oxy-fuel coating, electrophoretic deposition, laser ablation, hydrothermal and biomimetic methods. However, the cracking of the coating under mechanical forces has not been considered in these prior art reports.

Therefore, there is need to develop a process for effective coating on to implant surface which will significantly improve the cracking resistance of coating under mechanical forces. Accordingly, the present invention provides an effective process, which combines two conventional processing techniques: dip coating and electrospinning, to give a uniform, non-cracking coating on implant surfaces.

OBJECTIVE OF THE INVENTION

The main objective of the present invention is to provide a process for obtaining an implant with a biocompatible polymer coating by using sequential dip coating followed by electrospinning process.

SUMMARY OF THE INVENTION

Accordingly the present invention provides a process for obtaining an implant with a biocompatible polymer coating, said process comprising:
(a) dipping the implant in a solution of biocompatible polymer to obtain an implant with a dip coating; and
(b) immediately electrospinning the same polymer onto the implant with dip coating of step (a) to obtain an implant with a biocompatible polymer coating;
wherein, fibres of the biocompatible polymer are partially embedded into the dip coating, and said coating remains intact/independent of cracks/tears even after application of mechanical forces selected from the group consisting of bending, tensile stress, compression, and torsion.

In another embodiment of the present invention, the biocompatible polymer is selected from the group consisting of silk fibroin, polylactic acid (PLA), poly ε-caprolactone (PCL), and collagen.

In still another embodiment of the present invention, the implant is made up of a material selected from the group consisting of metal, polymer, ceramic, and composites thereof.

In another embodiment of the present invention the metal is titanium.

In yet another embodiment of the present invention the polymer is polydimethylsiloxane (PDMS) or polyethylene.

In still another embodiment of the present invention the ceramic is hydroxyapatite.

In another embodiment of the present invention, the implant is selected from the group consisting of breast implant, ocular implant, cardiovascular stent, and catheter tube.

In yet another embodiment of the present invention, the implant is in a form selected from the group consisting of tube, sheet, film, and 3D shape.

In still another embodiment of the present invention the thickness of said biocompatible polymer coating is in the range of 100 nm to 5 µm.

In yet another embodiment of the present invention the fiber diameter of said biocompatible polymer coating after electrospinning in the range of 100 nm to 1000 nm.

In another embodiment of the present invention the biocompatible polymer coating is modified with functional molecules, drugs, biomolecules, growth factors, proteins to enhance the effectiveness of the biocompatible polymer coating in biomedical applications.

Another embodiment of the present invention provides the process for coating the surface of polydimethylsiloxane (PDMS) implant with silk fibroin layer, wherein said process comprises the steps of:
  a) dipping polydimethylsiloxane (PDMS) implant in a solution of regenerated silk fibroin to obtain wet PDMS implant with regenerated silk fibroin coating;
  b) immediately placing the wet PDMS implant with regenerated silk fibroin coating of step (a) on collector of electro-spinning system;
  c) dissolving lyophilized silk fibroin (SF) in Hexafluroisopropanol (HFIP) to obtain a SF-HFIP solution;
  d) using the SF-HFIP solution of step (c) for electrospinning onto the wet PDMS implant with regenerated silk fibroin coating of step (b);
  e) randomizing deposition of electrospun fibers by aid of syringe translation and/or collector translation and/or rotation to obtain polydimethylsiloxane (PDMS) implant with silk fibroin layer.

Still another embodiment of the present invention provides an implant with a biocompatible polymer coating prepared by the aforementioned process.

DETAILED DESCRIPTION OF THE INVENTION

The invention will now be described in detail in connection with certain preferred and optional embodiments, so that various aspects thereof may be more fully understood and appreciated.

In the view of above, the present invention provides a novel process to coat the surface of flexible polymeric implant with biocompatible polymer such that the coating does not crack when the implant is subjected to mechanical forces such as tension, torsion or bending while retaining the inherent properties of the coated polymer.

Accordingly the present invention provides a process for obtaining an implant with a biocompatible polymer coating, said process comprising:
  (a) dipping the implant in a solution of biocompatible polymer to obtain an implant with a dip coating; and
  (b) immediately electrospinning the same polymer onto the implant with dip coating of step (a) to obtain an implant with a biocompatible polymer coating;
    wherein, fibres of the biocompatible polymer are partially embedded into the dip coating, and said coating remains intact/independent of cracks/tears even after application of mechanical forces selected from the group consisting of bending, tensile stress, compression, and torsion.

In one embodiment of the present invention, the electrospinning is directly done onto a dip coated wet substrate. As a result of which some fibers are embedded into the dip coated layer, while others on the surface are not embedded. The combination of this partial embedment and lower thickness of coating helps in preventing cracking. In another embodiment, the present inventors also prepared a coated implant where the fibers are completely embedded in a coating of silk fibroin as suggested from prior art, it is observed that the coating does not meet the cracking resistance requirements and results are as shown in example 1.

In another embodiment of the present invention, the biocompatible polymer is selected from the group consisting of silk fibroin, polylactic acid (PLA), poly ε-caprolactone (PCL), and collagen.

In yet another embodiment of the present invention, the biocompatible polymer is silk fibroin.

In still another embodiment of the present invention, the implant is made up of a material selected from the group consisting of metal, polymer, ceramic, and composites thereof.

In another embodiment of the present invention the metal is titanium.

In yet another embodiment of the present invention the polymer is polydimethylsiloxane (PDMS) or polyethylene.

In still another embodiment of the present invention the ceramic is hydroxyapatite.

In another embodiment of the present invention, the implant is selected from the group consisting of breast implant, ocular implant, cardiovascular stent, and catheter tube.

In yet another embodiment of the present invention, the implant is in a form selected from the group consisting of tube, sheet, film, and 3D shape.

In still another embodiment of the present invention the thickness of said biocompatible polymer coating is in the range of 100 nm to 5 µm. In yet another embodiment of the present invention the fiber diameter of said biocompatible polymer coating after electrospinning in the range of 100 nm to 1000 nm. The implant undergoes deformation when subjected to tensile strength, compression, torsion or bending forces during handling and/or use.

In another embodiment of the present invention the biocompatible polymer coating is modified with functional molecules, drugs, biomolecules, growth factors, proteins to enhance the effectiveness of the biocompatible polymer coating in biomedical applications.

Another embodiment of the present invention provides the process for coating the surface of polydimethylsiloxane (PDMS) implant with silk fibroin layer, wherein said process comprises the steps of:
  a) dipping polydimethylsiloxane (PDMS) implant in a solution of regenerated silk fibroin to obtain wet PDMS implant with regenerated silk fibroin coating;
  b) immediately placing the wet PDMS implant with regenerated silk fibroin coating of step (a) on collector of electro-spinning system;
  c) dissolving lyophilized silk fibroin (SF) in Hexafluroisopropanol (HFIP) to obtain a SF-HFIP solution;
  d) using the SF-HFIP solution of step (c) for electrospinning onto the wet PDMS implant with regenerated silk fibroin coating of step (b);
  e) randomizing deposition of electrospun fibers by aid of syringe translation and/or collector translation and/or rotation to obtain polydimethylsiloxane (PDMS) implant with silk fibroin layer.

The SEM analysis of the dip coating showed a thickness of ~400 nm. The coatings are found to be uniform and continuous. However, it is observed that the coating on these discs cracked after bending. The bending protocol followed is as per that given in the literature.

Still another embodiment of the present invention provides an implant with a biocompatible polymer coating prepared by the aforementioned process.

Silk fibroin is electrospun onto the dip-coated samples in wet condition. This process ensured embedding of silk fibroin nano-fibers into the RSF matrix, which led to achieve a classical self-reinforced fiber composite system.

Figure 1:
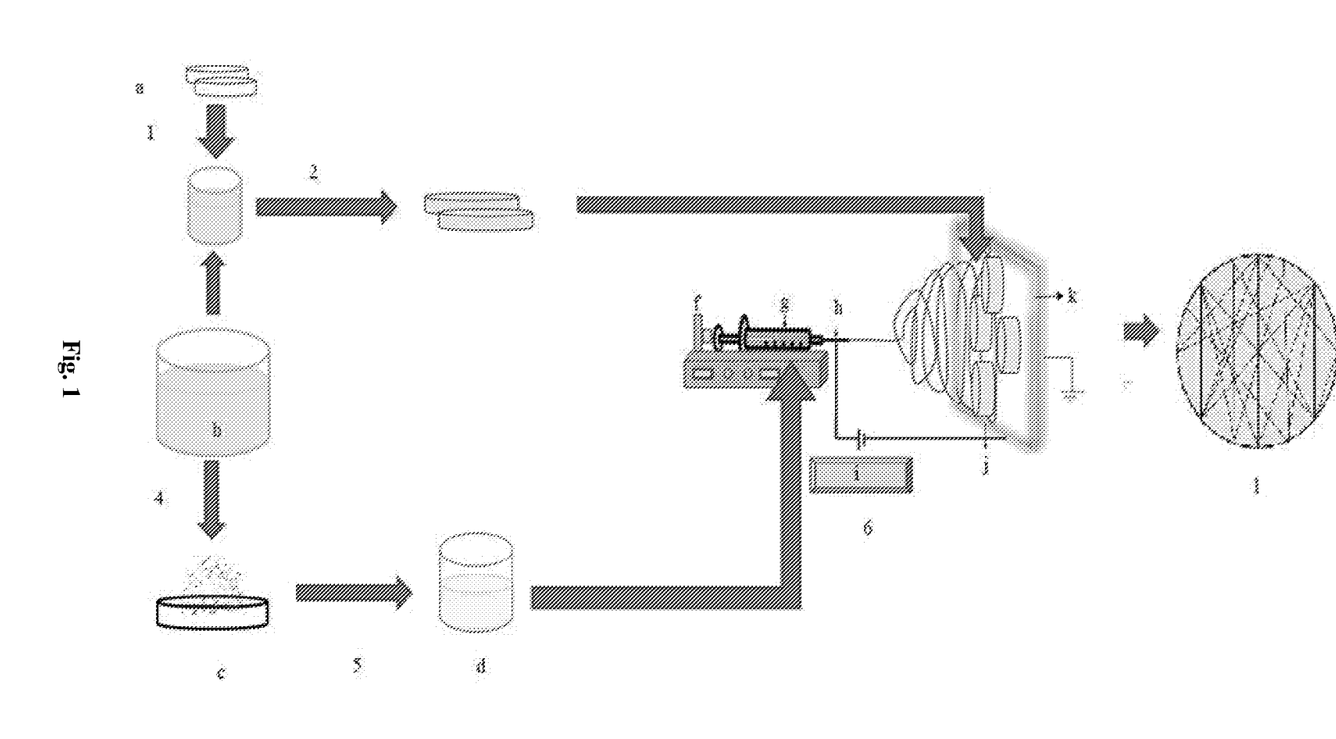
FIG. 1: Schematic representation of the procedure for making self reinforced SF coatings.
  a—PDMS disc; b—Polymer solution; c—Polymer powder; d—solution of polymer; f—syringe pump; g—syringe; h—needle; i—voltage unit; j—wet PDMS disc stuck onto the collector; k—collector; l—PDMS disc with dip and electrospun fibers obtained,
  1—Process of dip coating the PDMS disc in polymer solution; 2—Dip coated PDMS disc transferred to the collector; 4—Polymer powder obtained by a process like lyophilization; 5—Dissolution of polymer powder at particular concentration in suitable solvent; 6—Process of electrospinning
Figure 2:
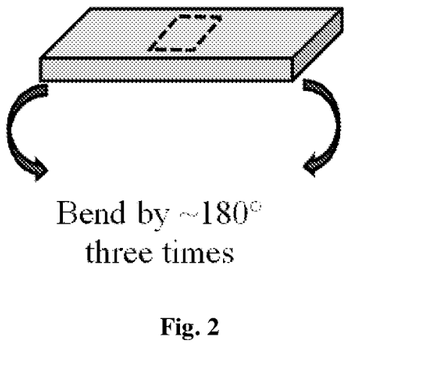
FIG. 2: Schematic representation of bending stability test.
Figure 3:
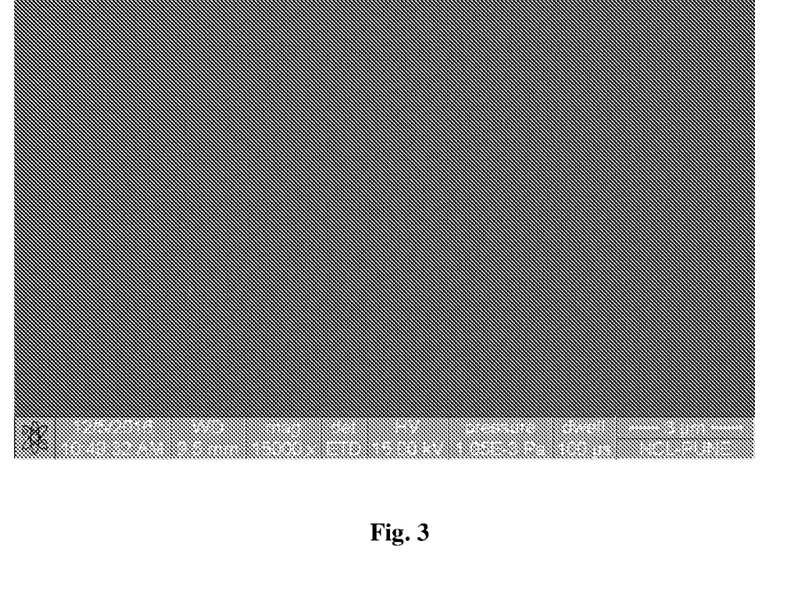
FIG. 3: Scanning electron micrograph Dip coated sample before bending.

From FIG. 3 it is observed that regenerated silk fibroin forms a continuous coat onto PDMS discs after dip coating and drying. The coat shows no macro or micro cracks and/or any deformities when observed under the scanning electron microscope.

Figure 4:
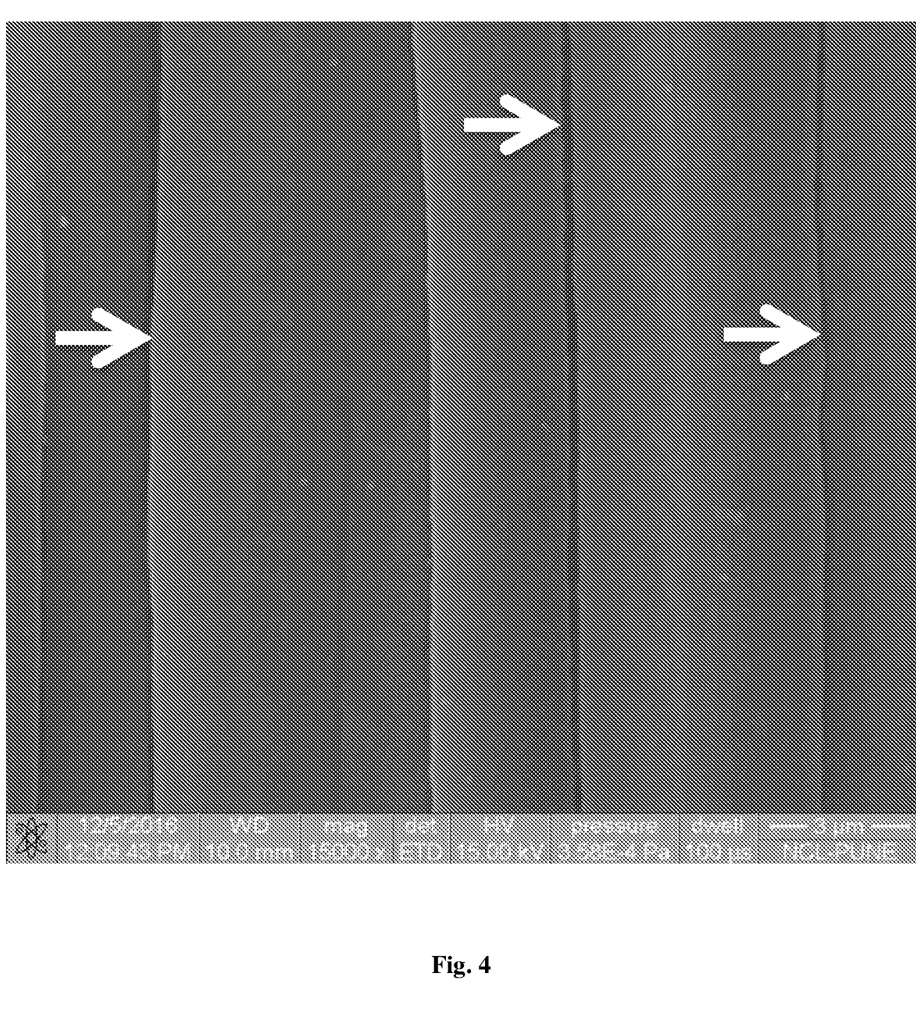
FIG. 4: Scanning electron micrograph Dip coated sample after bending.

From FIG. 4 it is observed that when the silk fibroin dip coated PDMS discs were subjected to bending, the coating near the central region showed cracking in the direction perpendicular to bending. The cracks are indicated by arrows in the Figure.

Figure 5:
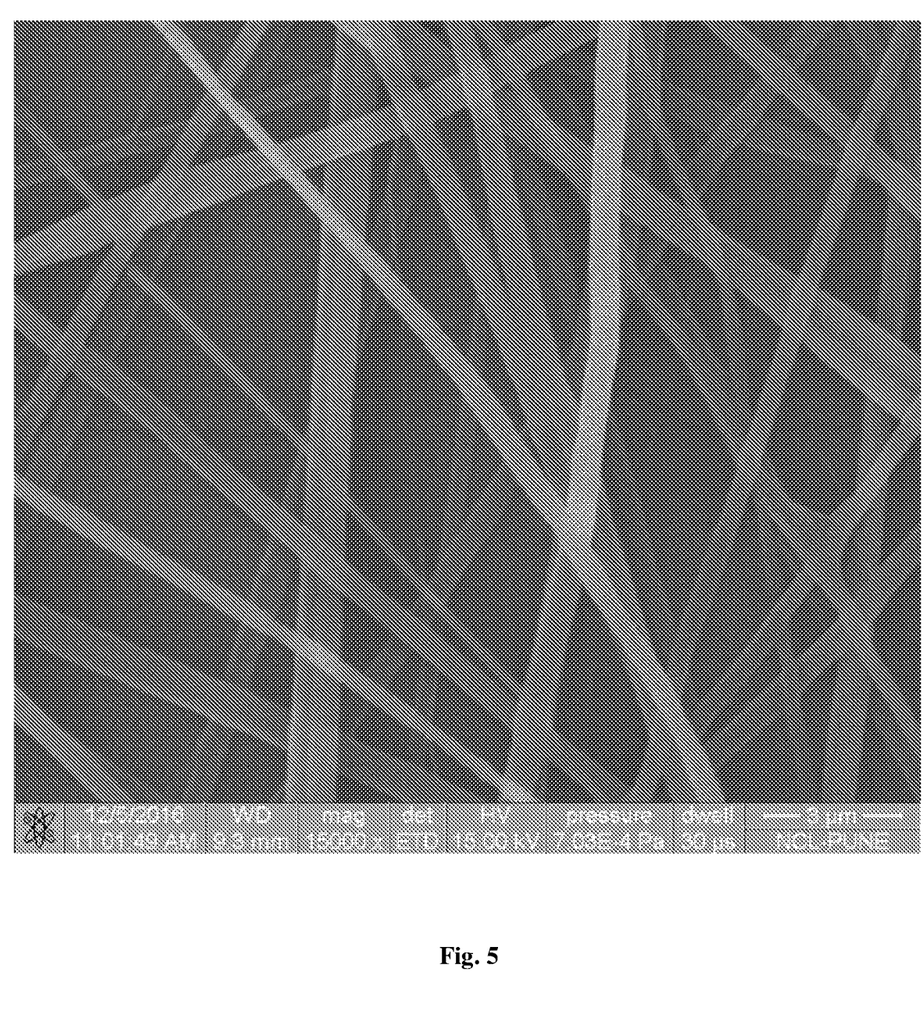
FIG. 5: Scanning electron micrograph Dip coated+electrospun (self-reinforced) sample before bending.

From FIG. 5 it is observed that on the PDMS discs that were subjected to sequential dip coating and electrospinning, there was a continuous silk fibroin coat throughout. The electrospun fibers were partially embedded into the coat, providing a classical self-reinforced composite.

Figure 6:
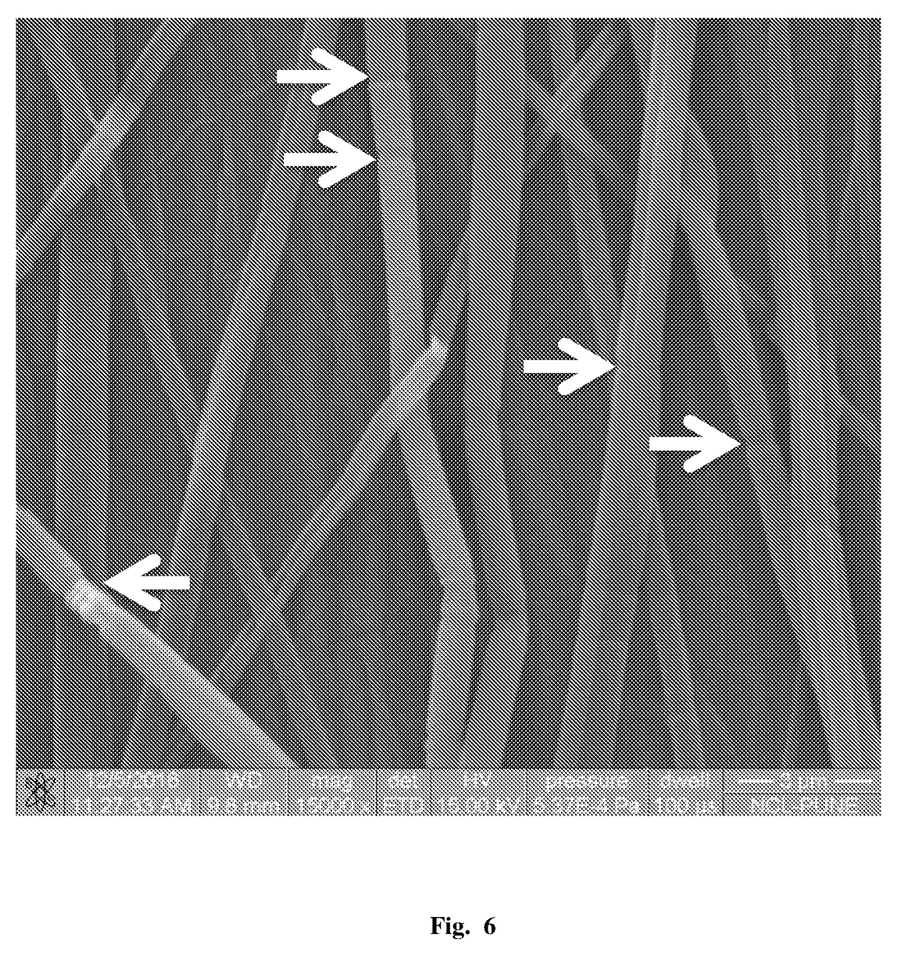
FIG. 6: Scanning electron micrograph Dip coated+electrospun (self-reinforced) sample after bending.

From FIG. 6 it is observed that through scanning electron microscopy that PDMS samples with self-reinforced silk fibroin coating showed a continuous coat even after being subjected to bending. Also, it was observed that the fibers showed thinning at certain places along the length, which indicates that the fibers took up the load. The arrows indicate regions of deformation observed in the fibers supporting the fact that the fibers bear the load during bending.

Figure 7:
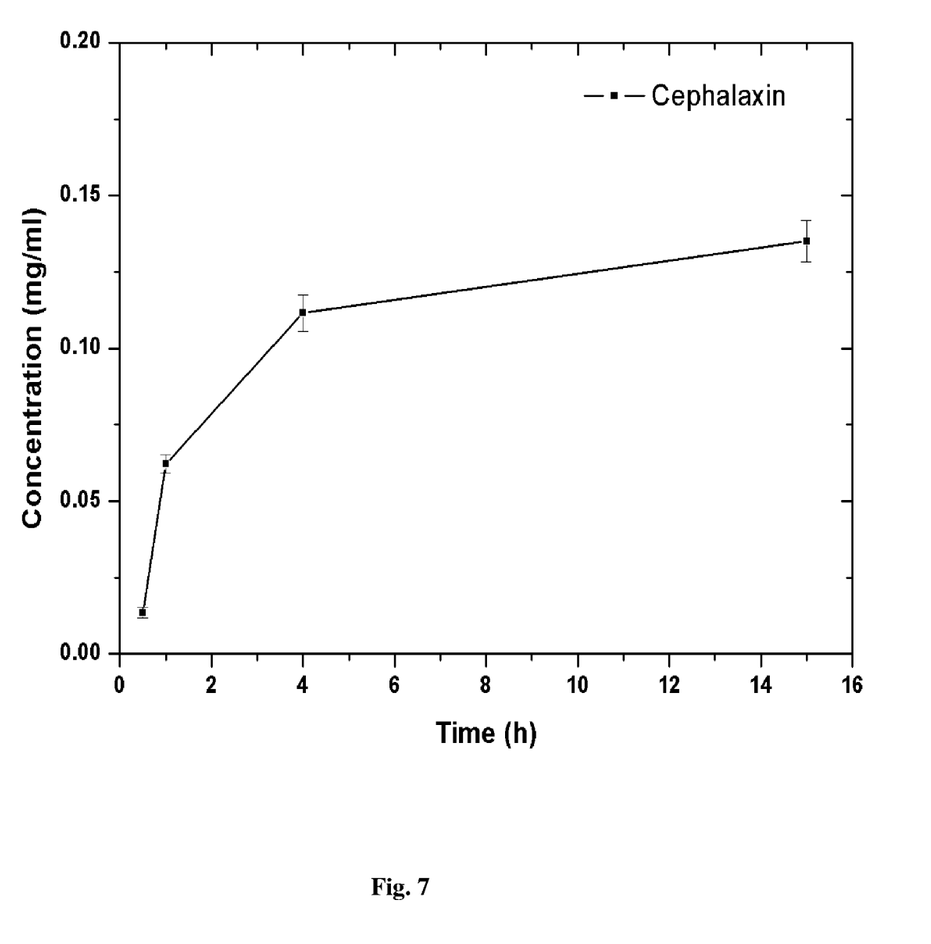
FIG. 7: Release of Cephalexin into DI water at 25° C. over a time period of 15 h.

In UV spectroscopy, the signature peak of 262 nm for cephalexin is monitored and as shown in FIG. 7, the coating enabled continuous release of this molecule over a period of 15 h.

Figure 8:
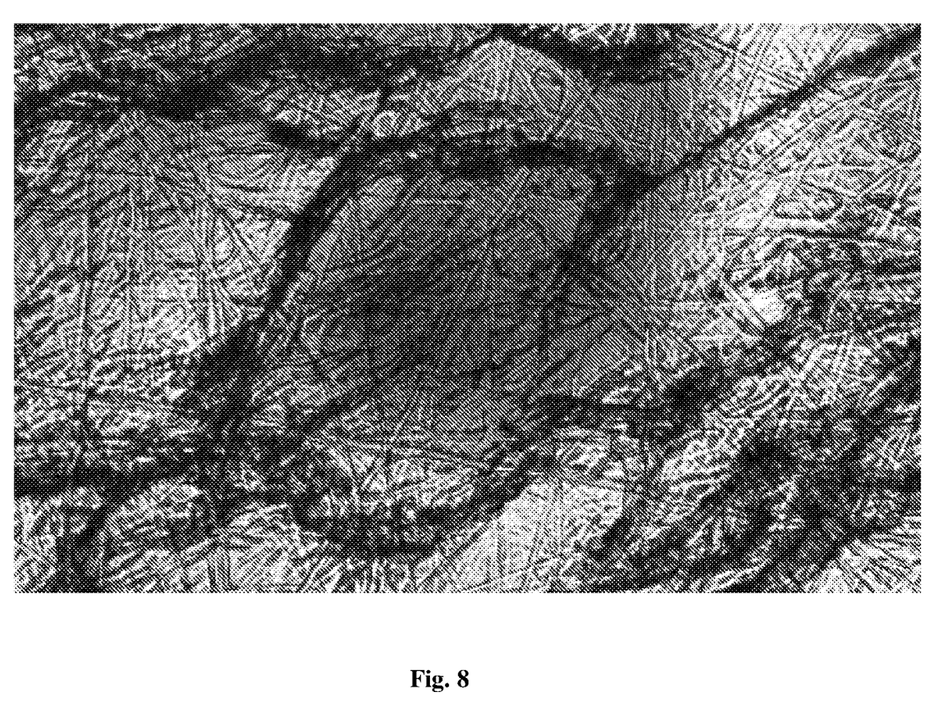
FIG. 8: Optical microscopy image after bending stability test on sample prepared as per protocol described in Example 7.

The FIG. 8 shows that when the fibers are completely embedded in a coating of silk fibroin as suggested from prior art, the coating does not meet the cracking resistance requirements and it shows cracks.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Preparation of Regenerated Silk Fibroin (RSF) Solution

*Bombyx mori* silk cocoons were procured from Central Sericultural Research and Training Institute, Srirampura, Manandavadi Road, Mysore-570008, India. They were cut and degummed (sericin removal) by boiling in 0.5% w/v solution of sodium bi-carbonate ($NaHCO_3$) (Thomas Baker). The silk fibroin obtained was dried for 48 h under vacuum at 60° C., −720 mmHg. The dried silk fibroin was cut and dissolved in 9.3 M aq. solution of Lithium Bromide (Sigma) at 60° C. for 4 h. This solution was dialysed against deionised water for 48 h. The solution was centrifuged for 30 min at 10000 rpm, to remove any impurities or insoluble materials. The supernatant (RSF) was transfer into clean containers and was stored under 4° C. until further required (Maximum storage period is 8 days). The concentration of RSF solution was between 3% to 8% w/v. This solution was split into two parts. The concentration of one part was adjusted to 0.4% w/v by addition of deionised water. This was store under 4° C. and later used as the dipping solution. The second part was quenched in liquid nitrogen and was lyophilised at −55° C. for 8 h. The aerogel thus obtained was stored under −18° C. until further required.

Example 2: Preparation of Polydimethyl Siloxane (PDMS) Discs for Coating

PDMS was obtained as a 2 part kit (Sylgard 184, Dow Corning). The resin and cross-linker were mixed in 10:1 ratio, by weight. The mixture was poured into polystyrene petriplates and kept in a vacuum oven, 40° C., −720 mmHg, for 24 h. The cured PDMS discs were peeled off and cut into 30 mm×10 mm rectangles using a scalpel. The cut specimens were cleaned in isopropyl alcohol (Merck) under continuous sonication for 20 min. The specimens were then kept in a vacuum oven at 60° C., −720 mmHg for 24 h. The dried discs were subjected to oxygen plasma at RF power 50 W, for 1 min. The plasma treated discs were stored under deionised water until further required.

Example 3: Dip Coating PDMS Using RSF

Plasma treated PDMS discs (Example 2) were taken out from the deionised water and then dipped into 0.4% w/v RSF solution (Example 1) for 10 min. The discs were then taken out and dried at 25° C. under ambient conditions.

Example 4: Sequential Dip Coating+Electrospinning onto PDMS

Lyophilised RSF (Example 1) was dissolved into hexafluroisopropanol (HFIP) (Gujrat Flurachemical Pvt.

Ltd.), under continuous stirring, to obtain a 3% w/v solution. This solution was poured into a 5 ml disposable syringe (Dispovan), whose needle was blunted.

Plasma treated PDMS (Example 2) discs were taken out from the deionised water and then dipped into 0.4% w/v RSF solution for 10 min. The discs were taken out and placed on an aluminium foil in the wet condition. This foil was attached to the plate collector of the electrospinning setup, ensuring good contact between the foil and the collector. Ground terminal of the electrospinning setup was attached to the collector.

The syringe with SF-HFIP solution was placed on the syringe pump of the electrospinning setup and the live terminal was attached to its needle. Electrospinning was done onto the discs in the wet condition with the following parameters:

Distance between the collector plate and the needle tip: 10.5 cm
Needle gauge: 24
Pump speed: 1.5 ml/h
Voltage: 25 kV
Syringe translation: 0.98 m/s
Plate translation: Syringe translation linked After 3.5 h of electrospinning, the discs were carefully removed and place in a methanol (Merck) bath for 10 min. After this methanol treatment, the discs were kept in a vacuum oven, 60° C., −720 mmHg, for 24 h, to remove the methanol.

Example 5: Bending Stability of the Coating

Samples from Example 3 and Example 4 were divided into two sets each. One set was kept as it was while the other set was subjected to bending deformation. This was done by holding the two ends of the specimen, along the 30 mm axis, between the thumb and the index finger; and bending the samples along the axis till the two ends met. This was repeated three times on each sample of the set. The protocol followed is as described by Borkner et al. A 10 mm×10 mm square was observed under a scanning electron micrograph to study the coating surface. As seen in FIG. 6, the fibers exhibit areas of stress whitening, indicating that the fibers take up the load applied during bending. However, the coating remains intact and the substrate surface is not exposed. The arrows indicate regions of deformation observed in the fibers supporting the fact that the fibers bear the load during bending.

Example 6: Sequential Dip Coating+Electrospinning onto PDMS Using Drug Molecule Lyophilized RSF (Example 1) (30 mg) and Cephalexin (30 mg) (a standard antibiotic) was dissolved into 1 ml of hexafluroisopropanol (HFIP) (Gujarat Fluorochemicals Pvt. Ltd.) with mild stirring for 10 minutes. 2 ml of this solution was then used for electrospinning onto RSF dip coated PDMS discs (15 mm diameter) using the same electrospinning conditions as described in Example 4. After 3 h of electrospinning, the PDMS discs were carefully removed and annealed in water vapor at 95° C. for 2 h. One annealed PDMS disc was then dipped in 1 ml DI water at 25° C. for 15 h and the release of cephalexin in DI water was measured. In UV spectroscopy, the signature peak of 262 nm of cephalexin was monitored and as shown in FIG. 7, the coating enabled continuous release of this molecule over a period of 15 h.

Example 7: Sequential Dip Coating+Electrospinning+Dip onto PDMS as Suggested from WO2017093181

The samples obtained in Example 4 were further dipped in a 0.4 w/v % solution for 10 minutes and air-dried at room temperature. The coating thickness obtained using this method was found to be in the range of 5-10 microns. This sample was then subjected to the bending stability test as described in Example 5. As can be seen in FIG. 8, the coating completely cracks at several locations and is not stable under bending loads. A thin coating (100-1000 nm) with only partially embedded polymeric fibers in the dip coat will produce a stable coating resistant to mechanical forces such as bending.

ADVANTAGES OF THE INVENTION

The present invention provides a novel, cost effective, efficient process to coat the surface of implant with biocompatible polymers such that the coating does not crack when subjected to mechanical forces such as bending, compression, tensile or torsion while retaining the inherent properties of the biocompatible polymer.

We claim:

1. A process for obtaining an implant with a biocompatible polymer coating, said process consisting of:
    (a) dipping an implant in a solution comprising a first biocompatible polymer to obtain an implant with a wet dip coating comprising the first biocompatible polymer; and
    (b) electrospinning a second biocompatible polymer onto the implant with the wet dip coating of step (a) to obtain an implant with a biocompatible polymer coating comprising the first biocompatible polymer and electrospun fibers of the second biocompatible polymer; wherein
        a portion of the fibers of the second biocompatible polymer are embedded into the dip coating and another portion of the fibers of the second biocompatible polymer are not embedded into the dip coating, and
        the biocompatible polymer coating remains intact, without the formation of cracks or tears after application of a mechanical force selected from the group consisting of bending, tensile stress, compression and torsion.

2. The process as claimed in claim 1, wherein the first biocompatible polymer and the second biocompatible polymer are selected from the group consisting of silk fibroin, polylactic acid (PLA), poly ε-caprolactone (PCL), and collagen.

3. The process as claimed in claim 2, wherein at least one of the first biocompatible polymer and the second biocompatible polymer is silk fibroin.

4. The process as claimed in claim 1, wherein said implant is made up of a material selected from the group consisting of metals, polymers, ceramics, and composites thereof.

5. The process as claimed in claim 4, wherein said implant is made of a metal.

6. The process as claimed in claim 5, wherein the metal is titanium.

7. The process as claimed in claim 4, wherein said implant is made of a polymer.

8. The process as claimed in claim 7, wherein the polymer is polydimethylsiloxane (PDMS) or polyethylene.

9. The process as claimed in claim 4, wherein said implant is made of a ceramic.

10. The process as claimed in claim 9, wherein the ceramic is hydroxyapatite.

11. The process as claimed in claim 1, wherein said implant is selected from the group consisting of a breast implant, an ocular implant, a cardiovascular stent, and a catheter tube.

12. The process as claimed in claim 1, wherein said implant is in a form selected from the group consisting of a tube, a sheet, a film, and a 3D shape.

13. The process as claimed in claim 1, wherein the thickness of said biocompatible polymer coating is in the range of 100 nm to 5 µm.

14. The process as claimed in claim 1, wherein the fiber diameter of the electrospun fibers is in the range of 100 nm to 1000 nm.

15. The process as claimed in claim 1, wherein said biocompatible polymer coating includes at least one of a functional molecule, a drug, a biomolecule, a growth factor and a protein.

16. A process for coating the surface of a polydimethylsiloxane (PDMS) implant with a silk fibroin layer, said process consisting of:
   a) dipping a polydimethylsiloxane (PDMS) implant in a solution comprising regenerated silk fibroin to obtain a wet PDMS implant with a regenerated silk fibroin coating;
   b) placing the wet PDMS implant with the regenerated silk fibroin coating of step (a) on a collector of an electro-spinning system;
   c) dissolving lyophilized silk fibroin (SF), and optionally an antibiotic, in Hexafluroisopropanol (HFIP) to obtain a SF-HFIP solution;
   d) using the SF-HFIP solution of step (c) for electrospinning silk fibroin fibers onto the wet PDMS implant with the regenerated silk fibroin coating of step (b) and;
   e) randomizing deposition of the electrospun silk fibroin fibers by aid of syringe translation and/or collector translation and/or rotation to obtain the PDMS implant with a silk fibroin layer comprising the regenerated silk fibroin coating and the silk fibroin fibers; wherein
   a portion of the silk fibroin fibers are embedded into the regenerated silk fibroin coating and another portion of the silk fibroin fibers are not embedded into the silk fibroin coating, and
   the silk fibroin layer remains intact, without the formation of cracks or tears after application of a mechanical force selected from the group consisting of bending, tensile stress, compression and torsion.

17. The process of claim 16, wherein the lyophilized SF and the antibiotic are dissolved in HFIP to obtain the SF-HFIP solution step (c).

18. The process as claimed in claim 16, wherein said coating includes at least one of a functional molecule, a drug, a biomolecule, a growth factor and a protein.

19. The process of claim 1, wherein the first biocompatible polymer and the second biocompatible polymer are compositionally the same.

20. The process as claimed in claim 1, wherein the first biocompatible polymer is silk fibroin.

* * * * *